(12) United States Patent
Mühlau et al.

(10) Patent No.: US 9,078,822 B2
(45) Date of Patent: Jul. 14, 2015

(54) DRY LIPOSOMAL PVP-IODINE COMPOSITIONS

(75) Inventors: Silke Mühlau, Hamburg (DE); Wolfgang Fleischer, Ingelheim (DE)

(73) Assignee: Euro-Celtique S.A., Luxembourg (LU)

( * ) Notice: Subject to any disclaimer, the term of this patent is extended or adjusted under 35 U.S.C. 154(b) by 56 days.

(21) Appl. No.: 13/371,030

(22) Filed: Feb. 10, 2012

(65) Prior Publication Data

US 2012/0282323 A1    Nov. 8, 2012

Related U.S. Application Data

(63) Continuation of application No. 10/842,889, filed on May 10, 2004, now abandoned.

(30) Foreign Application Priority Data

May 19, 2003    (EP) ..................................... 03011027

(51) Int. Cl.
*A61K 9/127*    (2006.01)
(52) U.S. Cl.
CPC ..................................... *A61K 9/127* (2013.01)
(58) Field of Classification Search
None
See application file for complete search history.

(56) References Cited

U.S. PATENT DOCUMENTS

| | | |
|---|---|---|
| 3,687,855 A | 8/1972 | Halpern et al. |
| 4,113,857 A | 9/1978 | Shetty |
| 4,725,434 A | 2/1988 | Jauw |
| 4,996,048 A | 2/1991 | Bhagwat et al. |
| 5,078,987 A | 1/1992 | Nakamura et al. |
| 5,863,556 A | 1/1999 | Rückert et al. |
| 6,510,818 B2 | 1/2003 | Barney et al. |
| 7,297,344 B1 | 11/2007 | Fleischer et al. |
| 7,300,667 B1 | 11/2007 | Fleischer et al. |
| 7,364,749 B1 | 4/2008 | Fleischer et al. |
| 7,468,194 B1 | 12/2008 | Fleischer et al. |
| 2008/0038330 A1 | 2/2008 | Fleischer et al. |

FOREIGN PATENT DOCUMENTS

| | | |
|---|---|---|
| EP | 0 342 269 A2 | 11/1989 |
| EP | 0 371 283 A2 | 6/1990 |
| EP | 0 476 777 A1 | 3/1992 |
| EP | 0 526 695 A1 | 2/1993 |
| EP | 0 639 373 A1 | 2/1995 |
| EP | 0 823 996 | 2/1998 |
| GB | 2 084 464 | 4/1982 |
| JP | 2002-241287 | 8/2002 |
| WO | WO 95/15118 | 6/1995 |
| WO | WO 99/60998 | 12/1999 |
| WO | WO 99/60999 | 12/1999 |
| WO | WO 00/28969 | 5/2000 |

OTHER PUBLICATIONS

Edwards et al., 1997, "Large porous particles for pulmonary drug delivery," Science 276:1868-1871.
Müllinger et al., 1998, "Drugs delivered to the lung," Respiratory Drug Deliver, Abstracts IV, Hilton Head Island Conference, pp. 385-387.
Lauer et al., 1996. "Targeted delivery to the pilosebaceous unit via liposomes," Advanced Drug Delivery Reviews 18:311-324.
Talton et al., 1998, "Novel coating method for improved dry delivery," Univ. of Florida UF 1887.
Decision of Appeal issued on Nov. 5, 2013 in the file history of Japanese Application No. 2004-129590 (Appeal No. 2011-14812) (In Japanese with English translation).
Kumar et al., 2009, "Application of broad spectrum antiseptic povidone iodine as powerful action: a review". J. of Pharma. Sci. and Tech. 1(2):48-58.

*Primary Examiner* — Snigdha Maewall
(74) *Attorney, Agent, or Firm* — Jones Day (57) ABSTRACT

The present invention is directed to a storage stable package of a iodophor containing particulate pharmaceutically acceptable carrier compositions. The invention is particularly directed to a storage stable package of a PVP-iodine liposome compositions. The packaging material is generally plastic, paper or cardboard.

16 Claims, 8 Drawing Sheets

DRY LIPOSOMAL PVP-IODINE COMPOSITIONS

I. CROSS-REFERENCE TO RELATED APPLICATIONS

This application is a continuation of U.S. application Ser. No. 10/842,889, filed May 10, 2004, which claims priority benefits of European Application No. 03011027.4, filed May 19, 2003, the disclosure of each of which is incorporated herein in its entirety.

II. FIELD

The present invention is directed to a storage stable package of a iodophor containing particulate pharmaceutically acceptable carrier compositions. The invention is particularly directed to a storage stable package of a PVP-iodine liposome compositions. The packaging material is generally plastic, paper or cardboard.

III. BACKGROUND

Iodophors are well known germicidal agents comprising the combination of pharmaceutically acceptable, elemental iodine with an organic carrier selected from the group comprising, inter alia, povidone and cationic, anionic and non-ionic detergents.

Commercially available iodophor pharmaceutical preparations often have an inherent limitation of a sharp fall in titratable iodine content with subsequent loss in germicidal potency in storage. While many methods have been devised to obtain a substantially pure, stable iodophor product, products hitherto known in the art comprise variable quantities of iodides, which act to dissolve unreacted elemental iodine and serve as a catalyst for further autodegradation of the iodophor compound. This degradation of the iodophor compound and loss in titratable iodine content results in a lowered potency of pharmaceutical dosage forms containing these compounds and thereby limits the use of these agents for germicidal use.

It is known that when a iodophor compound is dissolved in aqueous or hydro-organic solvent, the level of titratable iodine will gradually decrease in the course of time, and that there will be an increase in the acidity of the iodophor solution. This lowering in titratable iodine content is the result of the well known reaction whereby the titratable iodine in aqueous solution reacts with hydrogen ions to form hydriodic acid which is a source of iodide ions. Thus, there is a catalytic conversion of available germicidal iodine to iodide ion over the course of time, resulting in a loss of germicidal potency as well as an increase in the solubilization of elemental iodine in its free form, thereby increasing the potential for irritation and toxicity.

While the loss of germicidal potency with time through the conversion of titratable iodine to iodide may be compensated by adding an excess of the iodophor compound at the time of manufacture of the pharmaceutical preparation, so as to constantly maintain a high level of titratable active germicidal iodine, this practice is costly as well as inherently contributory to a further increase of dissolved unreacted or loosely-bound elemental iodine in the solution, which contributes to possible noxious toxic responses.

Since in solution the iodophor complexed iodine, exerting microbicidal action, is in dynamic equilibrium with ionic iodine species, removal of one or more of the iodine species results in a reaction to restore said equilibrium. An extracting solvent removes or consumes iodine from the iodophor solution in a manner similar to that of a microbial and organic load during desinfecting use of the iodophor solution. The amount of iodine available for germicidal action in an iodophor preparation therefore is the amount of free iodine in equilibrium in the solution at the time of use. Such free or equilibrium iodine content represents the germicidal potency of the preparation, but not the total iodine content titrated for the preparation nor the apparent distribution of the iodine species. Although iodophor solutions have been assayed in the art for available or titratable iodine, it is the free or equilibrium iodine which is the particular form of iodine present in the iodophor solution that is instantly available to exert microbicidal action. This form of iodine differs from titratable iodine and the other iodine species present in the iodophor solution. Therefore, the equilibrium iodine content of an iodophor solution is to be distinguished from its titratable iodine content.

The titratable iodine content of an iodophor preparation includes the iodine reservoir of the iodophor preparation (povidone iodine), as well as the equilibrium iodine in solution:

Titratable iodine=Reservoir Iodine+Equilibrium Iodine

However, it is the equilibrium iodine alone that exerts the microbicidal action of the preparation at any given moment. The portion of the titratable iodine content remaining after subtracting the amount of equilibrium iodine present, serves as the iodine reservoir to generate new equilibrium iodine in solution as it is consumed by the microbial and bio-organic load in the course of microbicidal activity, but does not exert such germicidal action by itself.

Povidone-iodine (polyvinylpyrrolidone-iodine or PVP-I) of pharmaceutical grade is the raw material used in the preparation of PVP-I containing formulations. Povidone-iodine is a complex of iodine with povidone. It contains not less than 9.0% by weight, and not more than 12% by weight of available iodine (titratable iodine) calculated on a dry basis.

Iodophor solutions, notably povidone-iodine, have been packaged for medicinal use, e.g. in soft plastic material bottles or containers which can be used for various medicinal purposes, e.g. douching. However, a problem that has been encountered with such-packaged iodophor solutions, is that elemental iodine (equilibrium iodine) has leached into and even through the packaging material. This has resulted in a loss of active iodine and in a decrease in stability of the iodophor solution contained within the packaging, and has also made it difficult to handle such packaging since elemental iodine which has leached there through causes staining and irritation if touched. Elemental iodine not only reacts with the packaging material but also with other reactive ingredients, e.g. unsaturated compounds, of the iodophor preparation resulting in a loss of stability.

U.S. Pat. No. 4,113,857 discloses that when an amount of from 0.005 percent to 1.0 percent by weight of iodate ion is added to a selected quantity of povidone-iodine at the time of its manufacture, there is obtained a polymeric iodophor compound that is uniquely free of iodide ion content and exhibits a preferred stability in aqueous solution, so that the fall in the amount of titratable iodine on aging is greatly reduced whereby no excess quantity of iodophor is necessary in the manufacture of pharmaceutical preparations employing said iodophor product.

U.S. Pat. No. 4,996,048 discloses a method to minimize loss of iodine from an iodophor solution, notably polyvinylpyrrolidone iodophor, which is stored within a packaging, by providing a certain minimal level of additional iodide, in addition to the iodophor solution, which prevents or minimizes leaching of. iodine. through the- packaging itself. The separate introduction of additional iodide, above and apart from the iodide already present in the noted iodophor solution, reduces the leaching of any elemental iodine from the iodophor solution through the packaging.

EP 0526695 discloses storage stable PVP-I solutions useful for ophthalmic preparations containing an alkanizing agent, which however have to be packaged in glass bottles. Glass bottles are disadvantageous with regard to easy breaking and causing dangerous splinters.

EP 0639373 discloses particulate, especially liposomal, preparations for the external application of agents with antiseptic and/or wound healing promoting properties. The preparations are specifically applied to wounds, skin, mucous membranes and mucosa-like unkeratinized epithelial tissues of humans and animals. The use of antiseptics such as povidone iodine is disclosed. Liposomes are highly suited as carriers for antiseptic agents, especially for povidone iodine, and for agents promoting the healing of wounds and provide an extended and topical activity at the desired locus of action by interaction with cell surfaces. However, the issue of stability is not addressed.

Liposomes are well-known drug or compound carriers and thus the application of medicaments in liposomal- form has been the subject of investigation for quite some time. An overview concerning the administration of compounds in liposomal form to the skin is provided by the review Targeted delivery to the pilosebaceous unit via liposomes (Lauer, A. C. et al. (1996), Advanced Drug Delivery Reviews, 18, 311-324). This review describes the physical-chemical characterisation of liposomal preparations and their therapeutic applications for the treatment of the pilosebaceous unit. Compounds that have been investigated for delivery by liposomes include e.g. anti-cancer agents, peptides, enzymes, anti-asthmatic and anti-allergic compounds and, as mentioned above, also antibiotics.

Lately it has been found that liposomal antiseptic preparations of PVP-I can be used for the treatment of diseases of the upper and lower respiratory tract, as disclosed in WO 99/60998' and PCT/EP 99/03681. Such liposomal preparations can be lyophilized. However, the storage stability of the preparations is not addressed.

Further yet unpublished work of the applicant even revealed that these liposomal antiseptic preparations can additionally be used for the treatment of herpes, acne and other infective diseases of the skin.

There is still a need of storage stable iodophor containing preparations which do not necessarily need the addition of special stabilizers like iodide salts, iodate salts or alkanizing agents and can he stored for years. e.g. two years or even longer, in plastic material bottles and containers or even in paper or cardboard packages, without encountering the above-discussed leaching problems, and without having to use glass as a packaging material.

IV. SUMMARY OF THE INVENTION

According to the invention, the prior art problems are overcome by providing, a dry particulate iodophor containing composition, especially a lyophilised or freeze-dried composition, and providing a package comprising said dry composition in a plastic, paper or cardboard bottle, sachet, tube or container, as defined in claim 1.

The dependent claims define further advantageous embodiments of the invention.

The present invention provides a storage stable package of a particulate iodophor containing pharmaceutically acceptably carrier preparation in the form of a package of a dry particulate iodophor containing pharmaceutically acceptably carrier composition which can be reconstituted to give an applicable preparation. The preparation is suitable for e.g. promoting the healing of wounds, the treatment of herpes, acne and other skin infections or of diseases of the upper and lower respiratory tract and provides an extended and topical activity at the desired locus of action.

The packaging material comprises e.g. plastic material (hereinafter referred to as 37 plastic"), paper, cardboard or mixtures thereof and does not comprise glass. Preferably the package is a plastic bottle, container, sachet or tube. Suitable plastic materials comprise polypropylene (PP), Polyethylene (PE). cycloolefine copolymer (COC, e.g. Topas®), silicone, polytetra-fluoroethylene (PTFE, e.g. Teflon®), polyvinylchlorid (PVC), ethylene vinylalkohol (EVOH), polyethylene terephthalate (PET) or mixtures thereof. In certain embodiments of the invention, the package material is in the form of a film, foil, laminate film, or laminate foil comprising aforementioned polymers or mixtures thereof The plastic material may be of such a nature that it really reacts with, or gets stained by, elemental iodine or, iodine leaches through it under storage conditions. In some preferred embodiments the material would not be suitable for packaging iodophor containing preparations, unless the preparations are dry.

Preferably the iodophor is PVP-iodine.

It is one aspect of the present invention to provide a method of stabilising a particulate iodophor containing preparation for storage in plastic, paper and cardboard packages, preferably in plastic bottles or containers, by providing the same in form of a dry particulate iodophor containing composition. The dry composition can subsequently be transformed (reconstituted) into an applicable preparation.

In certain embodiments, stabilizers selected from the group of iodide salts, iodate salts and alkanizing agents are not used in the preparations. In other embodiments, stabilizers selected from the group of iodine salts, iodate salts and alkanizing agents are used in the preparations. Preferably, the iodate salts are used when the applicable preparation is a gel.

It is further an aspect of the present invention to provide a dry particulate iodophor containing compositions which can be stored with no significant degradation of the iodophor and no significant loss in titratable iodine content at temperatures up to at least 25° C./60% relative humidity, preferably at least 30° C./65% relative humidity in a plastic, paper or cardboard bottle, sachet, tube or container, without iodine leaching through.

In the most preferred embodiment, the dry particulate iodophor containing composition can be stored with no degradation of the iodophor and loss in titratable iodine content at temperatures up to at least 25° C. and 60% relative humidity, preferably at least 30° C., and 65% relative humidity in a plastic bottle, container, sachet or tube.

The packaging material needs to be substantially impermeable for humidity to be able to keep the composition dry. The material will be selected in accordance with the storage conditions. For rather dry conditions, the requirements for the material will be less, for high humidity conditions the material will have to be selected to be almost impermeable for water vapour. In case direct contact with water is possible, water impermeable materials will have to be selected. The package can be made of a single material, like a plastic film, or a composite material, like a laminate film.

Further disclosed is a method of storing a iodophor containing preparation as a dry composition in a plastic, paper or cardboard bottle, container, sachet or tube and preparing pharmaceutical preparation ready for application from the dry composition, useful to reduce the degradation of the iodophor and the loss in titratable iodine, comprising the steps of:
a) providing a iodophor containing particulate pharmaceutically acceptable carrier preparation,
b) freeze-drying the iodophor containing particulate pharmaceutically acceptable carrier preparation to obtain a dry composition.
c) placing the freeze-dried iodophor containing particulate pharmaceutically acceptable carrier composition in a plastic paper or cardboard bottle, container, sachet or tube to form a storage stable package,
d) before application, e.g. to a patient, mixing the freeze-dried iodophor containing composition with a pharmaceutically acceptable liquid medium to provide the applicable preparation.

An alternative method comprises the steps of
a) providing a iodophor containing particulate acceptable carrier preparation 1) and a separate mixture 2) comprising adjuvants and additives selected from the group of consistency-forming agents, viscosity-adjusting additives and emulgators;
b) freeze-drying the preparation 1) and the mixture 2);
c) blending the freeze dried preparation 1) and 2) to form a blended composition 3) and placing the blended composition 3) in a plastic, paper or cardboard bottle, container, sachet or tube to form a storage stable package;
d) before application, e.g. to a patient, mixing the blended composition 3) with a pharmaceutically acceptable liquid medium to provide the applicable preparation.

An alternative method comprises the steps of:
a) providing a particulate dispersion 1) and a mixture 2) comprising the iodophor, adjuvants and additives selected from the group of consistency-forming agents, viscosity-adjusting additives and emulgators;
b) freeze-drying the dispersion 1) and the mixture 2);
c) blending the freeze dried dispersion 1) and the freeze dried mixture 2) to form the blended composition 3) and placing the composition 3) in a plastic, paper or cardboard bottle, container, sachet or tube to form a storage stable package;
d) before application, e.g. to a patient, mixing the blended composition 3) with a pharmaceutically acceptable liquid medium to provide the applicable preparation.

Preferably the package comprises a plastic bottle, container, sachet or tube.

According to the present invention the mixing with the liquid medium can be accomplished via stirring or shaking. To enhance the mixing via shaking, beads can be included. A preferred embodiment is a package that contains two chambers, one for the dry composition and one for the liquid medium, which can be combined to give one mixture of the dry composition with the liquid medium.

VI. DETAILED DESCRIPTION

In the context of the present invention, the dry form of the liposome preparation is referred to as "composition", whereby the liposome preparation before drying and any reconstituted liposome preparations obtained from the dry composition and made up for application, are referred to as "preparations".

In the context of the present invention, "storage stable" means that substantially there are no loss of titratable iodine, no decomposition of the composition caused by the reaction of elemental iodine with other ingredients of the composition, no reaction of elemental iodine with the packaging material and no leaching of elemental iodine through the packaging material, when stored for years in a package that keeps the composition dry at normal storing conditions. Normal storing conditions in the context of the invention are up to about 25° C. and up to about 60% relative humidity.

In the context of the present invention the terms "lyophilised" and "freeze dried" are used equally.

Preparations for use in the invention can be produced by loading liposomes with PVP-iodine according to methods known in the art. The liposomal preparations described in EP 0 639 373 are one example. They can be administered in different fauns including, e.g. an ointment, a cream, a spray, a lotion, a solution, a suspension, a dispersion or a gel. The liposome preparations disclosed in EP 0 639 373 are incorporated herein by reference. WO 99/60998 and PCT/EP99/03681 also describe suitable liposome preparations. The liposome preparation disclosed in WO 99/60998 and PCT/EP99/03681 are also incorporated herein by reference. The dry compositions according to the invention may be obtained from the liposome preparations by drying, preferably freeze-drying. The dry composition can be transformed to the applicable preparation, by mixing with a suitable pharmaceutically acceptable medium such as physiological saline solution, distilled water and other such liquid media.

The preparations obtained from the dry compositions according to this invention often contain the active compound(s), such as PVP-iodine, encapsulated in the particulate carrier, especially in liposomes. In this it may occur that there is an amount of compound not encapsulated inside the carrier. The compound(s) may also be associated with the surface of the particulate carriers, as e.g. liposomes.

In certain preferred embodiments of the invention the major part, or even the whole amount, of the active compound(s) may be provided inside or outside the particulate carriers, as e.g. liposomes.

The preparations obtained from the dry compositions according to the invention then may show a marked initial effect which is observed in addition to the slower, protracted release of the active agent from the carrier. This effect is especially observed where the carrier comprises liposomes. Without wishing to be bound to any theoretical explanation, it is presently assumed that in addition to the iodophor encapsulated inside the liposomes, some iodophor is present outside of the liposomes, and probably loosely bound to the outer surfaces of the liposomes. This could be due to complex association of iodophor molecules with the liposomal membrane, or it could be due to active compound molecules forming a layer on the liposomal surface, which layer partly or even fully coats the liposome externally. The type and amount of this initial compound effect can e. g. be influenced by choice of the concentration parameters.

In the context of the present invention, protracted or prolonged release means that the active compound(s) is/are released from the pharmaceutical preparation, obtained from the dry compositions, over a time period up to 24 hours.

The association of iodophor compounds with liposomes, i.e. whether iodophors can be included in the interior of liposomes or, depending on the circumstances, can associate with the liposome surfaces, depends, among other things, on the components used for formation of the liposomes, as is well known from the above-mentioned references.

In a preferred embodiment, preparations obtained from the dry composition according to the invention may additionally comprise other anti-inflammatory agents and agents promoting wound-healing. These additional active agents may be present in the dry composition or may be added during the preparation of the applicable preparation from the dry composition.

These additional anti-inflammatory agents comprise e.g. phenolic compounds, detergents, alcohols, organic disinfectants including among other things formaldehyde-releasing compounds, phenolic compounds including alkyl and aryl phenolic compounds, as well as halogenated phenolic compounds chinolines, acridines, hexahydropyrimidines, quaternary ammonia compounds, iminium salts and guadinines. Agents promoting wound-healing comprise those substances that have been described in the literature for such applications. Such compounds comprise substances that are known for promoting the granulation and ephitelization. These include dexpanthenol, alantoines, azulenes, tunnins and vitamins; particularly from the vitamin B group, etc.

Inventive preparations obtained from the dry composition can also contain other customary agents including adjuvants and additives, antioxidants, conserving agents or consistency-forming agents such as viscosity-adjusting additives, emulgators, etc. The person skilled in the art will select these adjuvants and additives in such a way that the ability of preparations obtained from the dry composition, substantially consisting of particulate carriers such as liposomes and a iodophor, to comply with the intended application. Additives may also comprise salts that allow for the regeneration of the active compound, such as the released halogen atom in case of halogen-releasing compounds. In the case of PVP-iodine such an additive may be $KIO_3$. Other additives that mediate or enhance penetration of the. liposomes into the skin may also be part of the inventive preparations obtained from the dry compositions. Such additives comprise e.g. DMSO. These additional agents may be present in the dry composition or may be added during the preparation of the applicable preparation from the dry composition The amphiphilic substances generally known in prior art to form liposome membranes can be employed in the context of the invention as long as they are pharmaceutically acceptable for the intended application. Presently, liposome-forming systems comprising lecithin are preferred. Such systems can comprise hydrogenated soy bean lecithin besides cholesterol and disodium succinatehexahydrate. Usually one will make sure that the liposome-forming materials do not show any reactivity with the iodophor in order to ensure the required storage stability of commercial products. Due to its double-bond reactivity high cholesterol contents are usually avoided. However, for the preparation of the compositions of the present invention these compounds may be used since the dry compositions exhibit enhanced storage stability.

It is presently specifically preferred to use hydrogenated soy bean lecithin as the sole membrane-forming agent. Commercially available products such as Phospholipon® 90 H (Aventis, Germany) are also preferred.

As can be taken from the review of Lauer A. C. et al. 1955 (vide supra) phospholipid-based liposomes may also be generally used for production of liposomes that discharge their cargo into the skin. According to this review, the use of non-ionic liposomes, which can be formed with phosphatidylcholin, is also an option. Other components that may be used for the formation of micelles are also known to the person skilled in the art and may be used for the production of compositions according to the invention.

The known prior art methods for forming liposome structures can generally be used in the context of the invention. Broadly, these methods comprise mechanical agitation of a suitable mixture containing the membrane-forming substance and water or an aqueous solution. Filtration through suitable membranes is preferred in order to form a substantially uniform liposome size.

The average size of the liposomes according to this invention can vary over a broad range, generally from about 1 nm to about 100 μm. Liposomes or particulate carriers having diameters in the range of about 1 μm and 70 μm are preferred. The person skilled in the art knows that the efficiency of liposomal penetration into the skin increases with decreasing diameter and that therefore liposomes having diameters of about 1 μm to 10 μm, of about 5 to 7 μm or about 5 μm may also be used (Lauer et al., vide supra). Generally the size of liposomes should be selected such that a good penetration into the skin is guaranteed. A particularly preferred embodiment of the invention therefore comprises liposomes having a diameter of between about 1 and 25 μm.

Such liposomal preparations are then dried, e.g., lyophilized, to give the dry composition, which is subsequently packaged for storage.

Before use the dry compositions are mixed with a suitable pharmaceutical medium to form the applicable preparation. Such applicable preparations comprise gel-like formulations with medium or high viscosity, emulsions, dispersions, suspensions, solutions, ointments, waxes, sprays, lotions, etc.

Liposomes in more fluid preparations may be generally more suited for treatment of bacterial infections, while liposomes in more gel-like formulations are generally better suited for treatment of viral infections. It seems that symptoms that are due to viral infections are preferably treated with preparations according to the invention that allow for longer contact times with the affected body areas. Symptoms due to bacterial infections may be treated preferably with preparations that provide shorter contact times with the affected body areas.

A preferred preparation, obtainable from the dry composition, comprises liposomes in a gel-like preparation such as a gel of medium to high viscosity, waxes or an ointment. Additionally these preparations preferably comprise liposomes of rather large size such as liposomes having a diameter of between about 1 μm and 30 μm, preferably between about 10 μm and 30 μm, more preferably between 20 μm and 30 μm and most preferably at around 25 μm. The formulation as a Hydrogel is preferred. If in the context use is made of the term "gel", this thus always includes a Hydrogel.

Generally, liposomes having a rather small average diameter are better suited for production of solutions, dispersions, suspensions. Such rather small diameters typically comprise diameters of around 1 μm to 10 μm, or even smaller in the case of solutions. In contrast, gel or ointment formulations may comprise liposome of a size of up to 50 μm.

Where alternative particulate carriers are used, they are generally prepared as known in the art. Thus, microspheres which are used to deliver a very wide range of therapeutic or cosmetic agents, are made as described for example in WO 95/15118.

Nanoparticles may in some cases be used, provided that they can be loaded with a sufficient amount of active agent. They can be prepared according to the methods known in the art, as e.g. described by Heyder (GSF München) in "Drugs delivered to the lung, Abstracts IV", Hilton Head Island Conference, May 1998.

Methods using a pulse laser deposition (PLD) apparatus and a polymeric target to apply coatings to drug powders in a short non-aqueous process are also suitable for the formation of particulate preparations according to this invention. These have e.g. been described by Talton et al., "Novel Coating Method for Improved Dry Delivery", Univ. of Florida UF 1887 (1998).

A further suitable delivery system employs Large Porous Particles as disclosed by David A. Edwards et al. in "Large Porous Particles for Pulmonary Drug Delivery" (Science, 20. June 1997, Vol. 276, p 1868-1871).

Generally, the concentrations in the preparation and dry composition, respectively, particle sizes, active agent loadings etc. will be selected for such alternative carriers to correspond basically to the parameters discussed herein with respect to liposome preparations. Selecting and providing such parameters based inter alia on straightforward experimentation, is well within the skill of an ordinary worker experienced in this art.

Generally, the amount of active agents in an inventive compositions will be determined by the desired effect on the one hand and the carrying capacity of the carrier preparation for the agent on the other hand. Broadly speaking, the amount of active agent in an inventive carrier composition can range in concentrations between the lower limit of effectiveness of the agent and the maximum loading of the agent in the respective carrier composition. It is understood that the iodophor compounds are present in the inventive compositions in a pharmaceutically sufficient amount. The dry composition will be compounded to result in applicable liposome preparations by adding a suitable amount of the pharmaceutically acceptable medium and exhibit the desired concentrations. 300 g of a dry liposome composition will usually contain between 3 to 200 g of the iodophor.

Suitable pharmaceutically acceptable media consist of or comprise media like water, oils, typical prior art ointment basis substances, gel-forming substances, e.g. agar, alginates, alginic acid, Arabic gum, gelatine, starch, tragacanth gum, methylcellulose, hydroxyethyl-cellulose, carboxymethylcellulose, polyvinylpyrrolidone (PVP) and polyacrylic acid and optionally usual auxiliary compounds. The pharmaceutically acceptable medium usually comprises all other ingredients necessary to result in the final applicable preparation upon mixing with the dry liposome composition. Alternatively all ingredients may be present in the dry composition and the applicable preparation is obtained solely by mixing with water, or some other liquid.

In a preferred embodiment the package comprises the dry, iodophor containing, particulate pharmaceutically acceptable carrier composition and separately a suitable amount of the pharmaceutically acceptable medium which is necessary to reconstitute the applicable preparation. Preferably the packages comprise beads, which enhance the mixing of the dry composition with the liquid medium to form the preparation. The beads are preferably made of ceramic, metal or plastic materials.

The final applicable preparation may be either mixed immediately before use or is mixed, stored and used in a certain time limit.

More specifically, for povidone iodine, a solution, dispersion, oil, ointment or gel in an inventive carrier preparation. especially where the carrier is a liposome preparation, can contain between 0.1 and 10 g of iodophor in 100 g of preparation. Such a preparation will then typically contain between 1 and 5 g of liposome membrane-forming substance especially lecithin, per 100 g of preparation.

Usually preferred iodophor compound concentrations such as of e.g. PVP-iodine concentration of the applicable preparation are normally between 1% to 10% and preferably 1% to 5% by weight.

In a lotion, which can be a hydrophilic or a lipophilic lotion, a typical range of PVP-iodine will be between 0.5 and 10 g compound, and between 1 and. 5 g, preferably about 4 g of liposome membrane forming agent such as hydrogenated soy bean lecithin per 100 g of lotion. In the case of a hydrophilic lotion, electrolyte solution will often be used in preparing the liposome-containing lotion.

A lipophilic lotion will often be made from compound, membrane-forming substance and lipophilic formation agents such as medium chain length triglycerides, etc.

A hydrophilic cream comprising an inventive liposome composition will generally comprise between 0.1 and 10 g PVP-iodine, together with between about 1 and 10 g membrane forming substance and further typical O/W cream forming additives per 100 g of cream.

A comparable amphiphilic cream according to the invention will have similar contents of agent and membrane forming substance such as lecithin, and will have the typical further additives of an amphiphilic cream.

A hydrophilic ointment according to the invention can broadly comprise between 0.1 and 10 g compound and between 1 and 10 g liposome membrane forming substance such as lecithin, together with typical prior art ointment basis substances such as Macrogol™ and water in 100 g of ointment.

A non-alcoholic hydrogel according to the invention could broadly comprise between 1 and 5 g PVP-iodine, approximately 2-4 g lecithin and gel-forming substances such as Carbopol®, with pH-adjusting agent and water to form 100 g of hydrogel.

An inventive aerosol or spray preparation will often comprise up to 50 mg, but could comprise up to and above 100 mg of liposomal active compound formulation per unit spray dose. The spray preparation will typically comprise at least 10% wt of PVP-iodine in the loaded liposomes (or alternative carrier particles), but may comprise up to 50% wt or even more of active agent. The amount of available iodine will generally be about 10% wt (based on PVP-iodine).

More specific formulations are notable from the embodiment examples.

The features and advantages of this invention will become clear in more detail from the ensuing description of preferred embodiments. In these embodiments, which include a best mode, povidone iodine is exemplified as iodophor and liposomes are chosen as the carrier. This should however not be construed as a restriction of this invention to povidone iodine, and/or to liposomes as the carrier, although such embodiments are specifically preferred. According to the invention other particulate carriers such as "large porous particles" or other micelles, nanoparticles, etc. can be formulated with agents like PVP-iodine.

One preferred method for producing the invention's dry liposomes can generally be described as follows:

The lipid membrane-forming components, e. g. lecithin, are dissolved in a suitable solvent such as chloroform or a 2:1 mixture of methanol and chloroform and are filtered under sterile conditions. A lipid film is then produced on a sterile high surface substrate, such as glass beads, by controlled evaporation of the solvent. In some cases, it can be quite sufficient to form the film on the inner surface of the vessel used in evaporating the solvent without using a specific substrate to increase the surface.

An aqueous system is prepared from electrolyte components and the (one or more) active agents to be incorporated in the liposome preparation. Such an aqueous system can e. g. comprise 10 mmol/l sodium hydrogen phosphate and 0.9% sodium chloride, at pH 7.4; the aqueous system will further comprise at least the desired amount of iodophor, which in the embodiment examples is povidone iodide. Often, the aqueous system will comprise an excess amount of agent or agents.

The liposomes are generally formed by agitating said aqueous system in the presence of said film formed by the lipid components. At this stage, further additives can be added to improve liposome formation; e. g. sodium cholate. Liposome formation can also be influenced by mechanical action such as pressure filtration through e. g. polycarbonate membranes, or centrifuging. Generally, the raw liposome dispersion will be washed, e. g. with electrolyte solution as used in preparing the above-described solution of the active agent.

When liposomes with the required size distribution have been obtained and washed, they can be redispersed in an electrolyte solution as already described, often also comprising sugars such as saccharose or a suitable sugar substitute. The dispersion is then dried, preferably lyophilized. Preferably, samples of 10-20 g each are freeze dried (freezing for 22 h at −20° C. and drying for 3 h at −40° C. and 0.5 mbar).

In a preferred embodiment, the preparation is a gel. The composition that can be made up for application as a gel can be prepared by the methods comprising: freeze drying of a liposomal PVP-I gel; freeze drying of polyacrylate gel, freeze drying of a mixture comprising PVP-I, $KIO_3$ and liposomes and blending the freeze dried polyacrylate gel and the freeze dried mixture comprising PVP-I, $KIO_3$ and liposomes; freeze drying a mixture comprising polyacrylate gel and liposomes, freeze drying of a PVP-I $KIO_3$ solution and blending the freeze dried mixture comprising polyacrylate gel and liposomes and the freeze dried PVP-I/$KIO_3$-solution; freeze drying a mixture comprising polyacrylate gel, PVP-I and $KIO_3$, freeze drying a liposomal dispersion and blending the freeze dried mixture comprising polyacrylate gel, PVP-I and $KIO_3$ and the freeze dried liposomal dispersion; freeze drying of a polyacrylate gel, PVP-I and $KIO_3$, freeze drying of a PVP-I/$KIO_3$ solution, freeze drying a liposomal dispersion and blending the freeze dried polyacrylate gel, PVP-I and $KIO_3$,- the freeze dried PVP-I/$KIO_3$ solution and the freeze dried liposomal dispersion. The blended mixtures can be tilled in a package as described herein.

The dry compositions can, prior to use, be made up for application by the addition of a suitable pharmaceutical acceptable medium. Preferably said suitable pharmaceutical acceptable medium is water.

The dry compositions can be stored in packages e.g. made of paper, cardboard or plastic for more than 2 years at temperatures up to 25° C. and 60% relative humidity, preferably 30° C. and 65% relative humidity. Preferably the composition is stored in a plastic bottle or container.

In the following Examples, hydrogenated soy bean lecithin (EPIKURON™ 200 SH obtainable from Lukas Meyer, Germany or PHOSPOLIPON™ 90 H (obtainable from Nattermann Phospholipid GmbH, Germany) was used. However, other pharmaceutically acceptable liposome membrane forming substances can be used instead, and the person skilled in the art will find it easy to select suitable alternative liposome forming systems from what is described in prior art.

The person skilled in the art is well aware that the liposomes-containing dispersion may comprise additional additives and adjuvants that can influence the appearance of the liposomal preparations. The inventive liposomal dispersion may contain e.g. colour pigments that ensure that the slightly yellow or brown colours that are due to PVP-iodine or released iodine are not visible. In the same manner liposomes or the pharmaceutical liposome-containing preparations may comprise additives that influence the consistency and the smell of the preparations.

The person skilled in the art is well aware that the choice of these additives and, adjuvants depends on the intended application form of the preparation (e.g. as ointment, gel or solution) and may be influenced by aesthetic considerations (such as colour and smell).

These additives may already be present in the dry composition or are later added with the pharmaceutical acceptable medium.

Examples are set out below that specifically illustrate the production of preferred embodiments of the invention. They are intended to illustrate how compositions according to the invention may be produced and they should by no means be read as limiting the invention to those examples.

Also, the use of unsaturated compounds like cholesterol will have to be carefully considered, since iodine may react with such unsaturated compounds. For many applications, only small amounts of such compounds will be employed, or liposomes will be used that can be formed in the absence of such compounds (as e.g. in the following Examples).

Embodiment Example I

In a 1000 ml glass flask, provided with glass beads for increased surface, 51.9 mg cholesterol and 213 mg hydrogenated soy bean lecithin were dissolved in a sufficient amount of a mixture of methanol and chloroform in a 2:1 ratio. The solvent was then evaporated under vacuum until a film was formed on the inner surface of the flask and on the glass beads.

2.4 g PVP iodine (containing about 10% available iodine) were separately dissolved in 12 ml water.

Again in a separate vessel. 8.77 g sodium chloride and 1.78 g $Na_2HPO_4.2H_2O$ were dissolved in 400 ml water. Further water was added up to a total volume of 980 ml, and then, approximately 12 ml 1 N hydrochloric acid were added to adjust pH to 7.4. This solution was then topped up with water to exactly 1000 ml.

In a fourth vessel, 900 mg saccharose and 57 mg disodium succinate were dissolved in 12 ml water.

The PVP iodine solution was then added to the lipid film in the flask and the mixture was shaken until the film dissolved. The resulting liposome formulation was separated from the hydrated lipids in the flask. The product was centrifuged and the supernatant liquid was discarded. The saccharose solution was added ad 12 ml and the product was again centrifuged. Afterwards the supernatant liquid was again discarded. At this stage, a further washing step, using the saccharose solution or the sodium chloride buffer solution could be carried out.

After the last centrifugation step and discarding of the supernatant, 12 ml sodium chloride buffer solution was added, and the liposomes were homogenously distributed therein. The product was then distributed into vials each containing 2 ml liposome dispersion, and the vials were then subjected to a freeze-drying step.

After the freeze-drying, each vial comprised about 40 mg solids.

The method of Embodiment Example I has a minor disadvantage in that the PVP iodine solution used, due to the high percentage of solids, is rather viscous and thus more difficult to handle.

Also the use of unsaturated compounds like cholesterol will have to be carefully considered, since iodine may react with such unsaturated compounds. For many applications, only small amounts of such compounds will be employed, or liposomes will be used that can be formed in the absence of such compounds (as e.g. in the following examples).

Embodiment Example II

In a 2000 ml flask provided with glass beads to increase surface, 173 mg hydrogenated soy bean lecithin and 90 mg disodium succinate were dissolved in approximately 60 ml of a methanol/chloroform mix in a 2:1 ratio. The solvent was removed under vacuum until a film was formed.

4 g PVP iodine (10% available iodine) were dissolved in 40 ml of the sodium chloride buffer solution described in Embodiment Example I, and were added to the lipid film in the flask. The flask was then shaken until the film dissolved and liposomes were formed.

The product was centrifuged and the supernatant liquid was discarded.

To the thus produced liposome pellet, further 40 ml sodium chloride buffer solution was added, and the centrifuging step was repeated. The supernatant was again discarded. At this stage, the washing step could be repeated where necessary.

After the final centrifuging and decanting step, 40 ml sodium chloride buffer solution was again added to the precipitated liposomes. The homogenous dispersion was then distributed into vials, each vial containing about 2 ml liposome dispersion, and the vials were then subjected to a freeze-drying step. This produced approximately 200 mg freeze-dried solids per vial.

The freeze dried compositions are placed in a polypropylene container for storage.

From the freeze-dried solid compositions of Examples I and II, further preparations were made as described in subsequent Embodiment Examples.

Like that of Embodiment Example I, the above-described method uses a hydrating step after film formation in the presence of organic solvents and aims at inclusion rates of 5 to 15%. These methods generally produce rather large and often multi-lamellar liposomes.

The above-described methods can be modified by a high pressure filtering step through a suitable membrane such as a polycarbonate membrane after the raw liposomes have been formed or after any of the subsequent washing steps or directly by using high pressure homogenization. This produces much smaller, unilamellar liposomes at increased amounts of encapsulated agent.

Instead of high pressure homogenization, other prior art methods known to provide small uniform sized liposomes can be employed.

Embodiment Example III

A hydrophilic (0/W) cream was prepared from 10 g hydrogenated soy bean lecithine/PVP iodine liposomes as described in Embodiment Example II; these were mixed with 4 g Polysorbate 40™, 8 g cetylstearyl alcohol, 8 g glycerol, 24 g white vaseline, and water ad 100 g.

Embodiment Example IV

An amphiphilic cream was prepared from 10 g hydrogenated soy bean lecithine/povidone iodine liposomes as described in Embodiment Example II; 7.5 g medium chain length tryglyceride, 7 g polyoxyethyleneglycerol monostearate, 6 g cetylstearyl alcohol, 8 g propylene glycol, 25 g white vaseline, and water ad 100 g.

Embodiment Example V

A hydrophilic ointment which can be rinsed off with water was prepared using 10 g of liposomal PVP iodine as described in Embodiment Example II, 55 g Macrogol 400™, 25 g Macrogol 4000™, and water ad 100 g.

Embodiment Example VI

A hydrogel was prepared from 4 g liposomal PVP iodine as described in Embodiment Example II, 0.5 g Carbopol® 980 NF™, sodium hydroxide ad pH 7.0, water ad 100 g. Further modifications of the above-described embodiments are envisaged.

Thus, the creams of Embodiment Examples IV and V can have an additional content of an agent known to promote the healing of wounds, such as allantoin.

Such an agent will be added in a pharmaceutically useful concentration, in the case of allantoin in the range of 0.1 to 0.5 g, per 100 g of cream. The wound healing agent can be incorporated in the cream base, in which case it will largely be outside the liposomes. It can, however, be partly or mostly incorporated in the liposomes, in which case it will be added at a corresponding suitable stage of the liposome composition method.

Similar alternatives are easily envisaged on the basis of the further Embodiment Examples.

For application of the inventive preparations to a patient, known systems can be used, such as pneumatic pump applicators, two-chamber gas pressure packs, aerosol spray dispensers etc.

In a pneumatic pump applicator, a bellows device is provided between an upstream and a downstream valve, both valves operating one way in the same direction. A supply of pharmaceutical preparation, such as an ointment or gel, is contained in a reservoir upstream of the valves-and-bellows device.

When compressing the bellows, the downstream valve opens and permits a dosed amount of preparation to leave the device for application. When the bellows is extended, this valve shuts and prevents reentry of the preparation. At the same time, the upstream valve opens and permits preparation from the reservoir to enter into the bellows, for release through the downstream valve upon the next compression step of the bellows.

The reservoir is sealed by a closure element which can move through the reservoir like a piston moves in a cylinder. By the stepwise emptying of the reservoir, this closure element is sucked into the reservoir so that the remaining amount of pharmaceutical preparation in the reservoir is always sealed off, while at the same time the reservoir can be emptied. Such a device is useful for pasty preparations creams, ointments etc.

In a two-chamber gas pressure pack, the pharmaceutical preparation is contained in a bag of flexible plastics film material. Often, this is high pressure polyethylene.

The bag is contained inside a gas tight pressure vessel which further contains a supply of pressurizing gas, very often a compressed inert gas like nitrogen or air.

The plastic film bag has only one outlet, which is gastightly connected to the interior wall of the pressure vessel, surrounding a single opening thereof. The pressurized gas in the vessel tends to compress the bag, driving the pharmaceutical preparation inside the bag out through the opening of the bag and thus through the opening of the vessel. A valve and, in case. spray-head device is provided in the vessel mouth.

Operating the valve releases a spray mist, a jet of liquid or a portion of flowable solid such as cream. Using such a system, solutions, emulsions, creams, ointments and gels can be dosed and applied.

Preferably, the applicators are designed to contain a separate chamber for the dry composition and a chamber for the liquid medium, which can be combined to obtain one chamber containing the dry composition and the liquid medium which via shaking give the applicable preparation. Preferably one of the chambers contains additionally beads of ceramic, metal or plastic materials to enhance the blending via shaking.

Embodiment Example VII

A dry liposomal composition was prepared. The amounts shown in Table 1 were used either for analytical or scale up compositions.

TABLE I

| Pos. | Substance | Amount (g/100 g) | Scale up (kg/1500 kg) |
|---|---|---|---|
| A | $H_2O$ | 15.0 | 200.0 |
| A | Phospolipon 90 H | 3.0 | 45.0 |
| B | $H_2O$ | 40.0 | 600.0 |
| B | Carbopol ® 980 NF | 1.5 | 22.5 |
| C | $H_2O$ | 2.0 | 30.0 |
| C | $KIO_3$ | 0.0708 | 1.09 |
| D | $H_2O$ | 20.0 | 300.0 |
| D | PVP-iodine 30/06 Avalaible iodine (10%) | 3.0 | 45.0 |
| E | $H_2O$ | 2.5 | 50.0 |
| F | $H_2O$ | 2.5 | 50.0 |
| G | $H_2O$ | 4.6 | 69.0 |
| G | NaOH solid | 0.46 | 6.9 |
| I | Citric acid, $H_2O$ free | 0.1065 | 1.059 |
| I | $Na_2(HPO)_4$, $H_2O$ free | 0.225 | 3.37 |
| I | $H_2O$ | 3.0 | 45.0 |
| H | $H_2O$ | ad 100.0 | ad 1500 |

Pos. stands for Position (see also below Table 2). Phospholipon® 90 H was purchased from Aventis (Germany). Carbopol® 980 NF was purchased from Noveon Inc. (USA) or Gattefosse (Germany) and PVP Iodine 30/06 was purchased from BASF (Germany).

Figure 1:
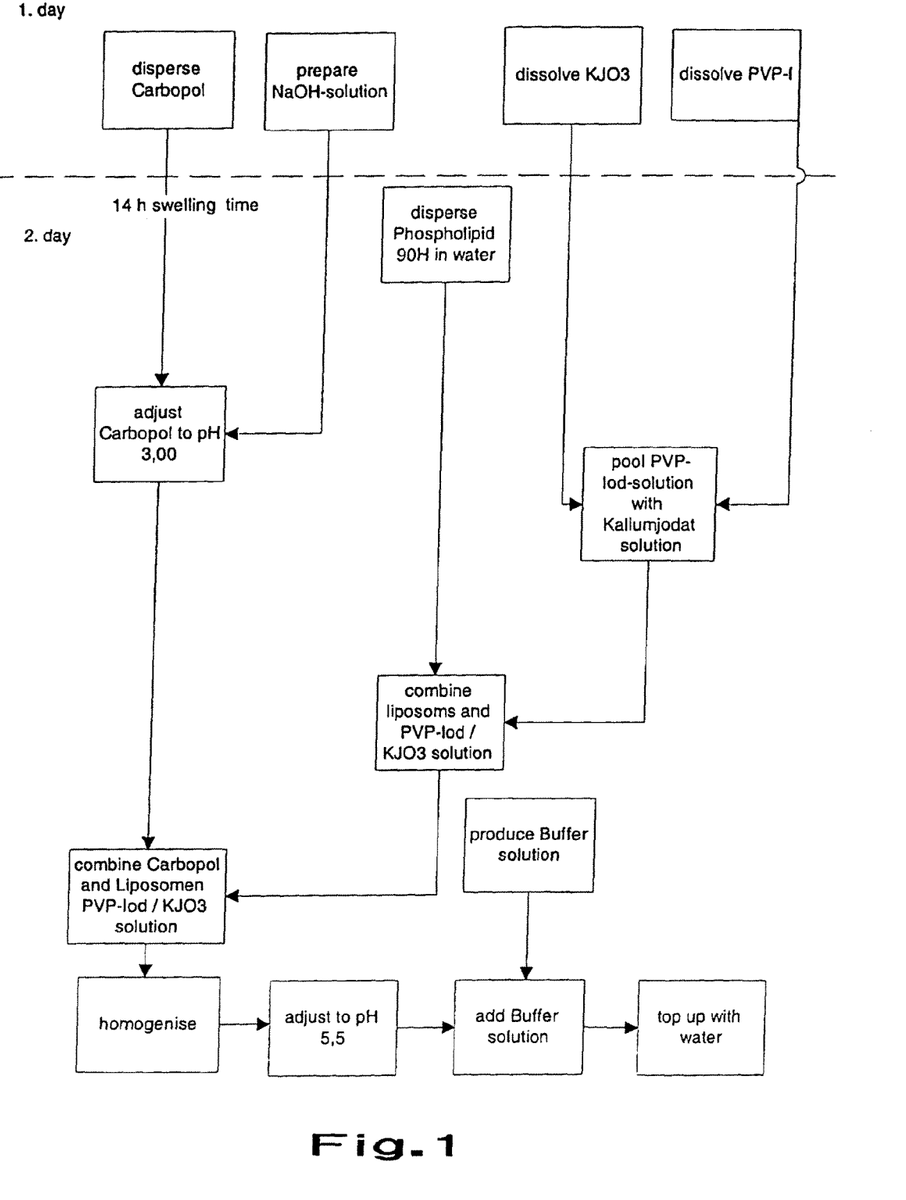
FIG. 1 shows the flowchart of a method for manufacturing a liposomal hydrogel formulation.
Figure 2:
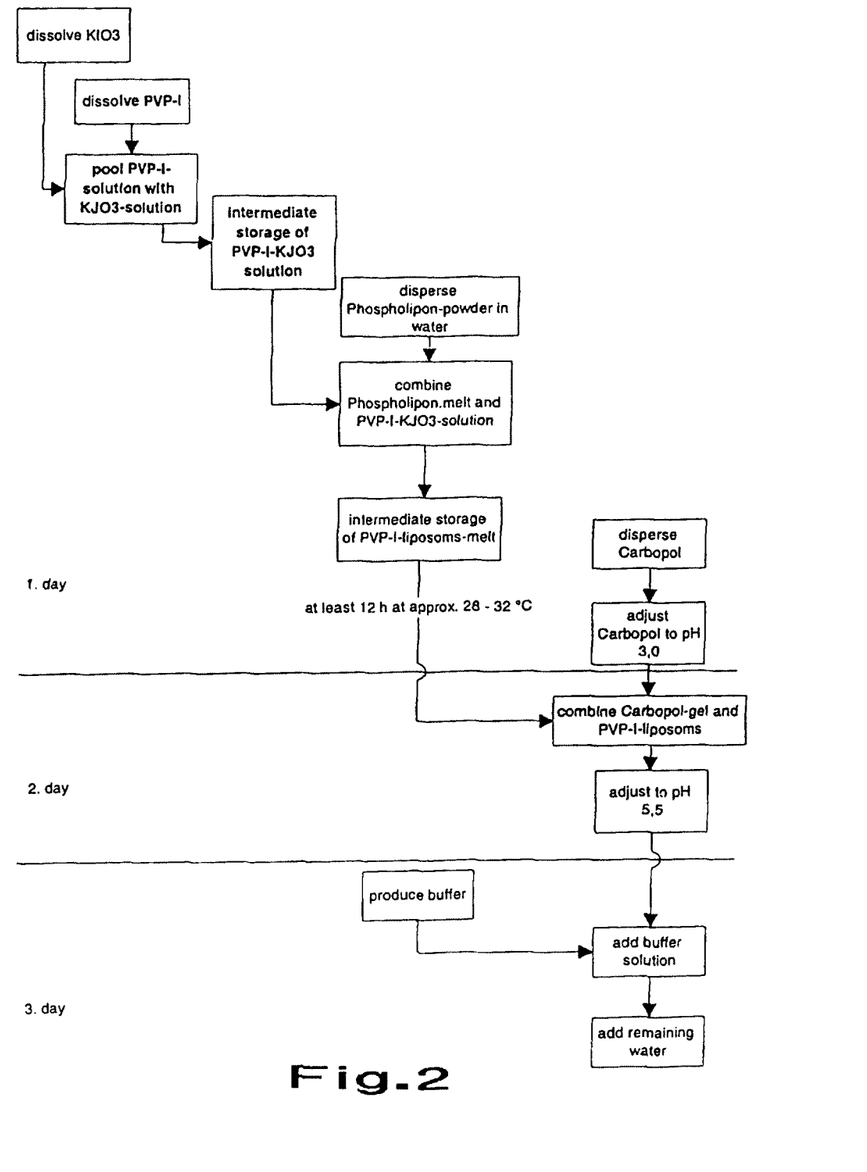
FIGS. 2-8 illustrate the flowcharts of alternative methods for manufacturing a liposomal hydrogel formulation.
Figure 3:
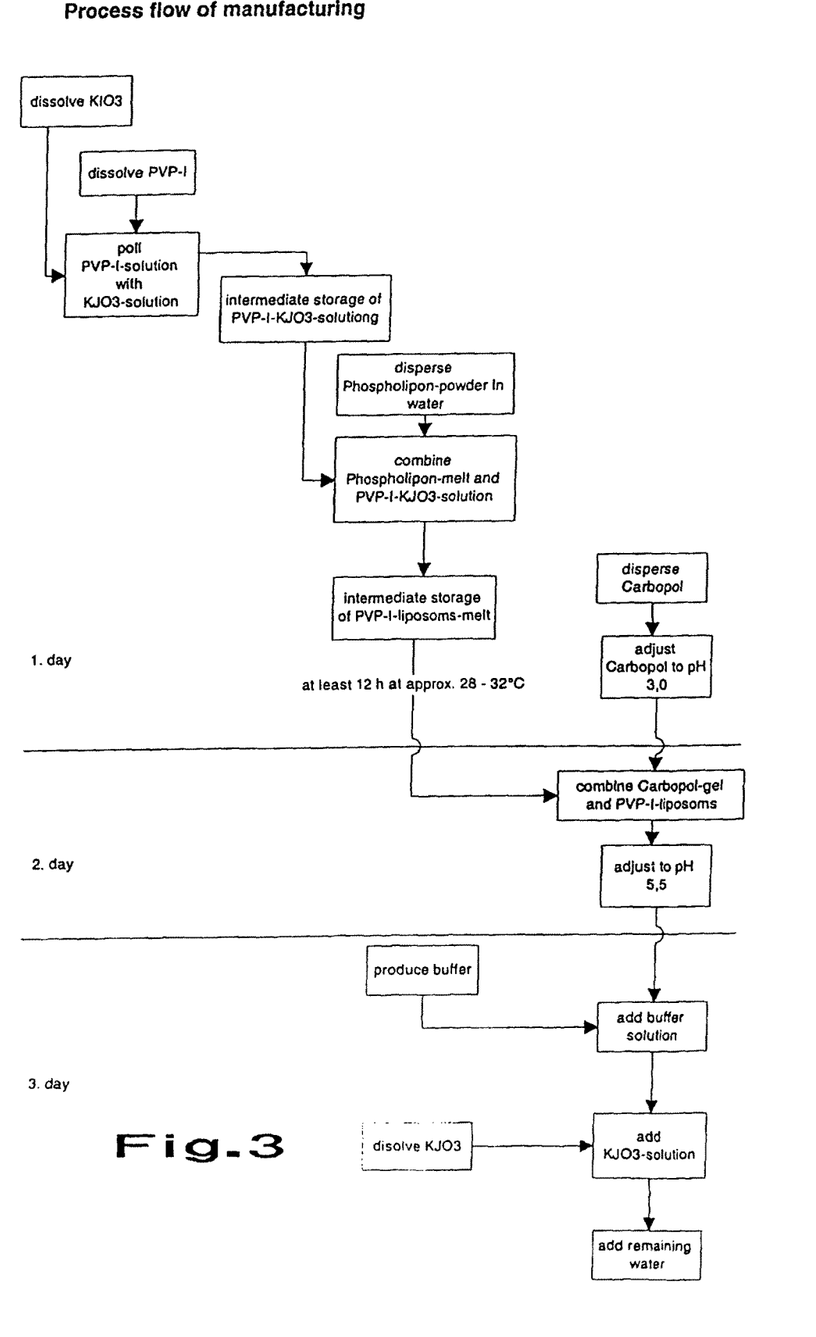
Figure 4:
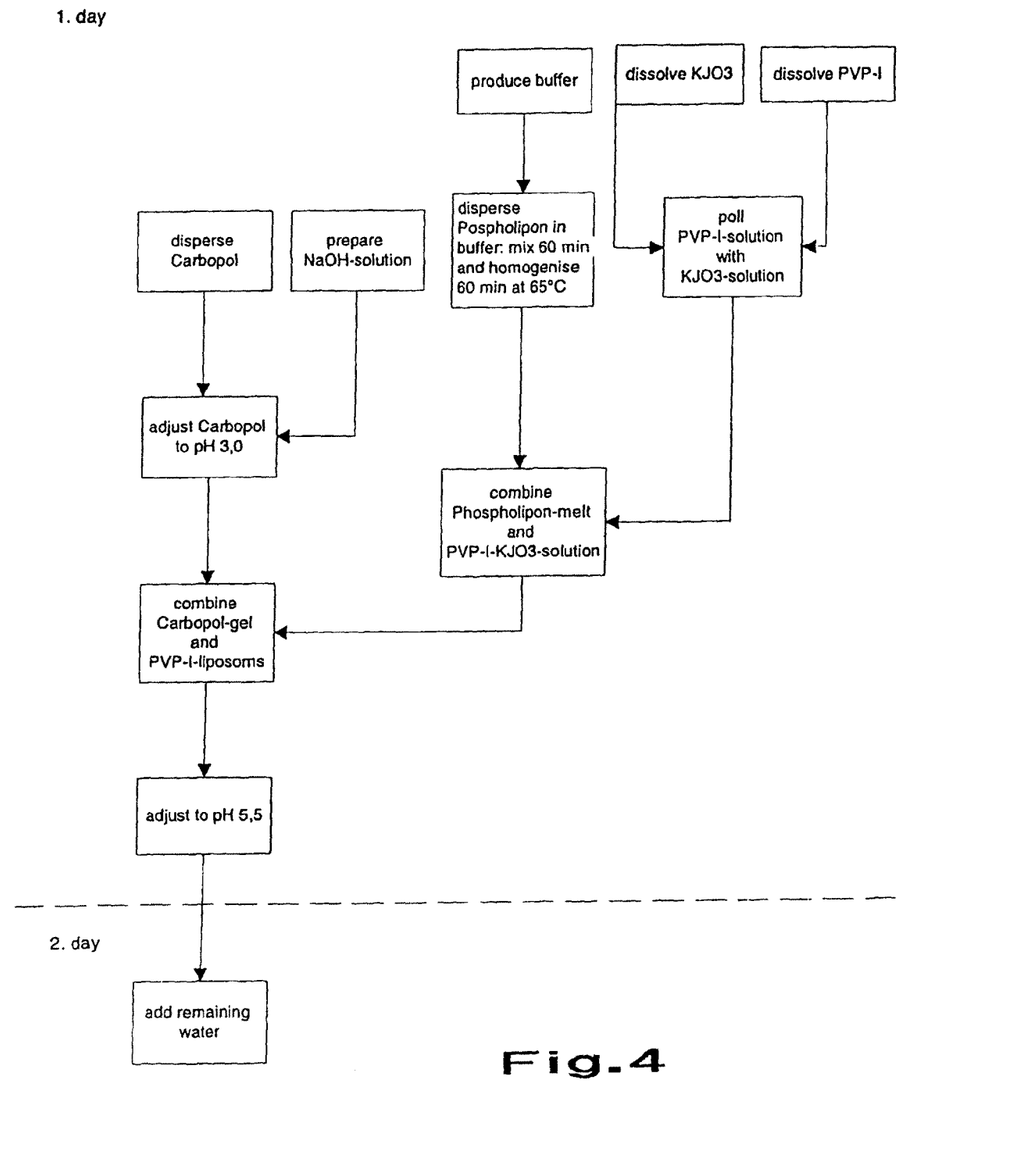
Figure 5:
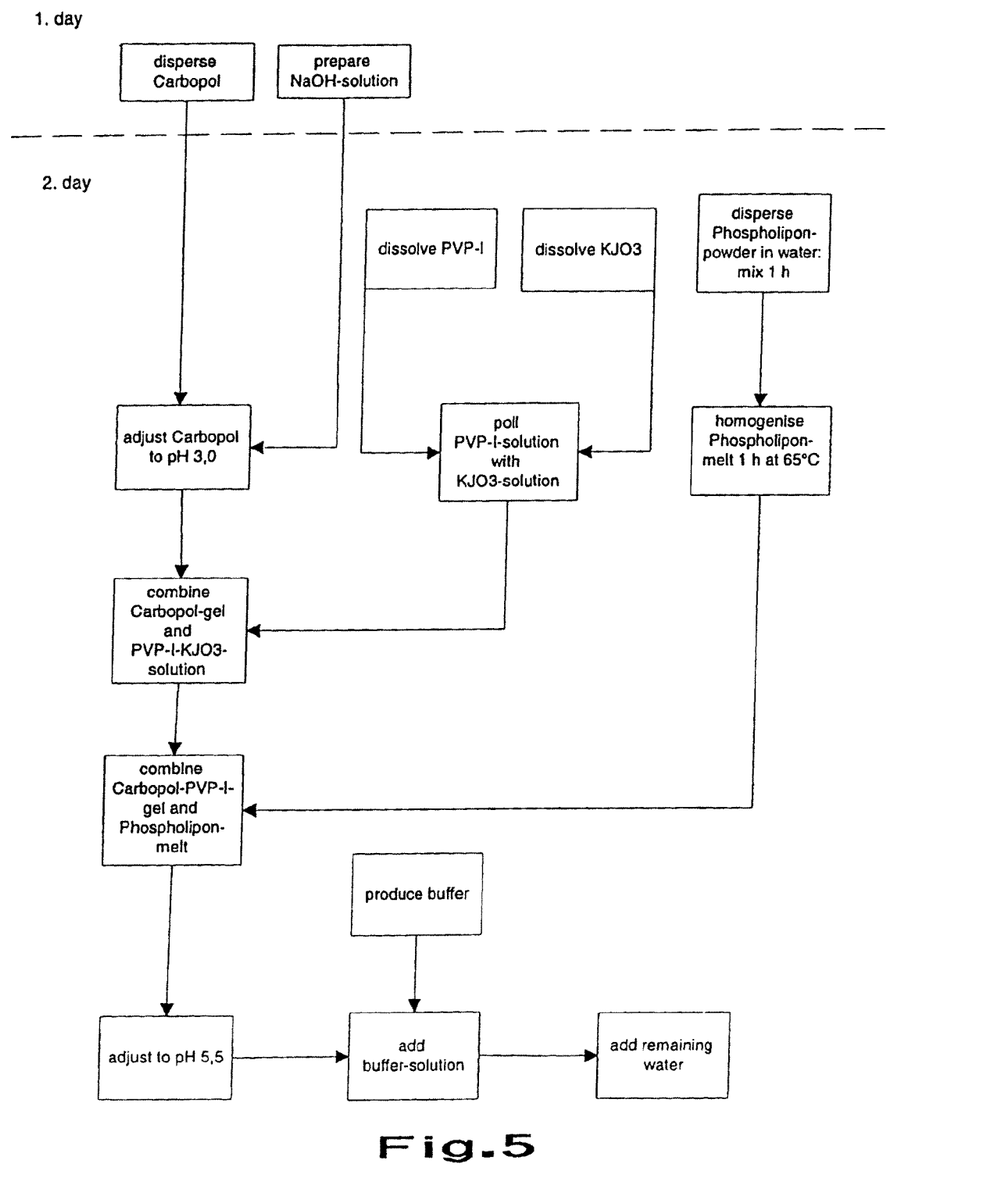
Figure 6:
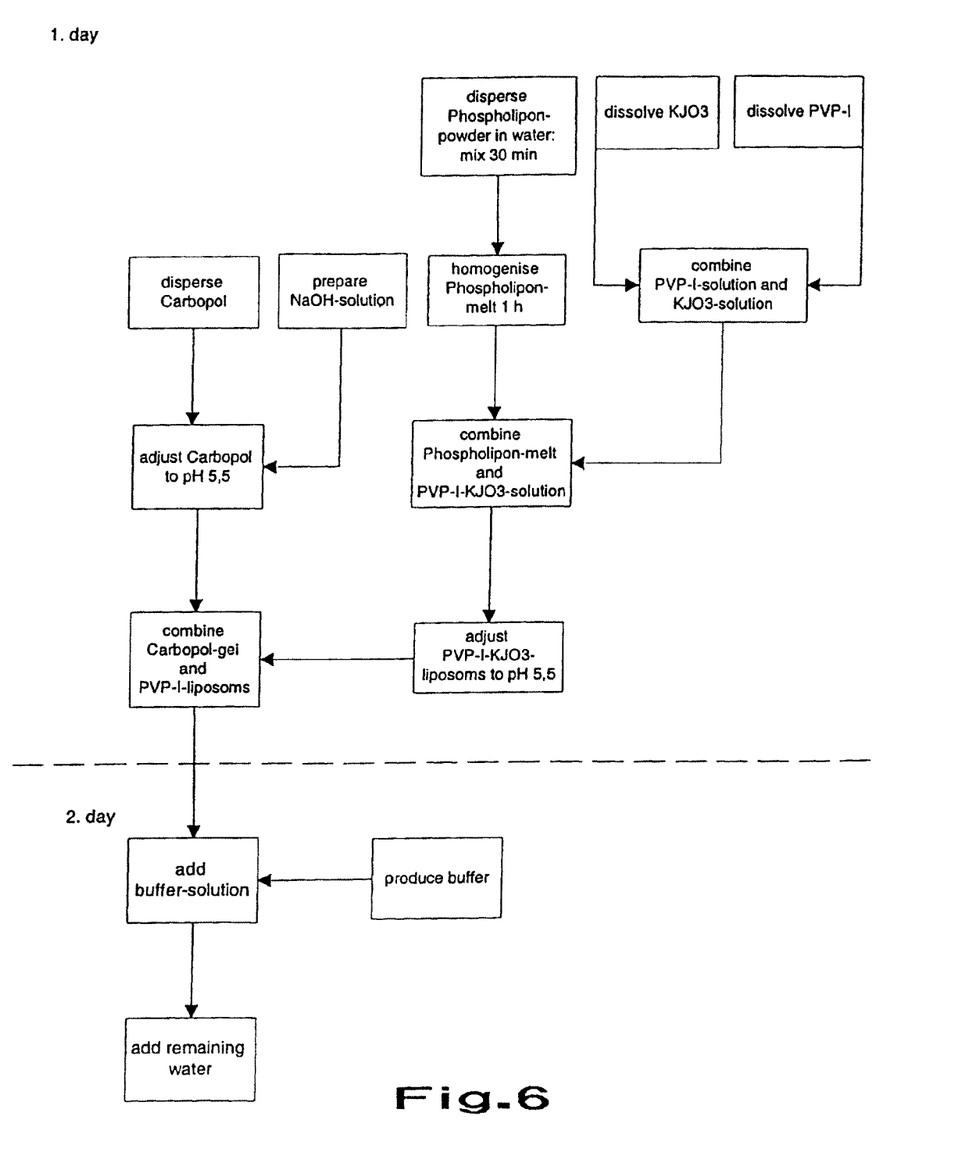
Figure 7:
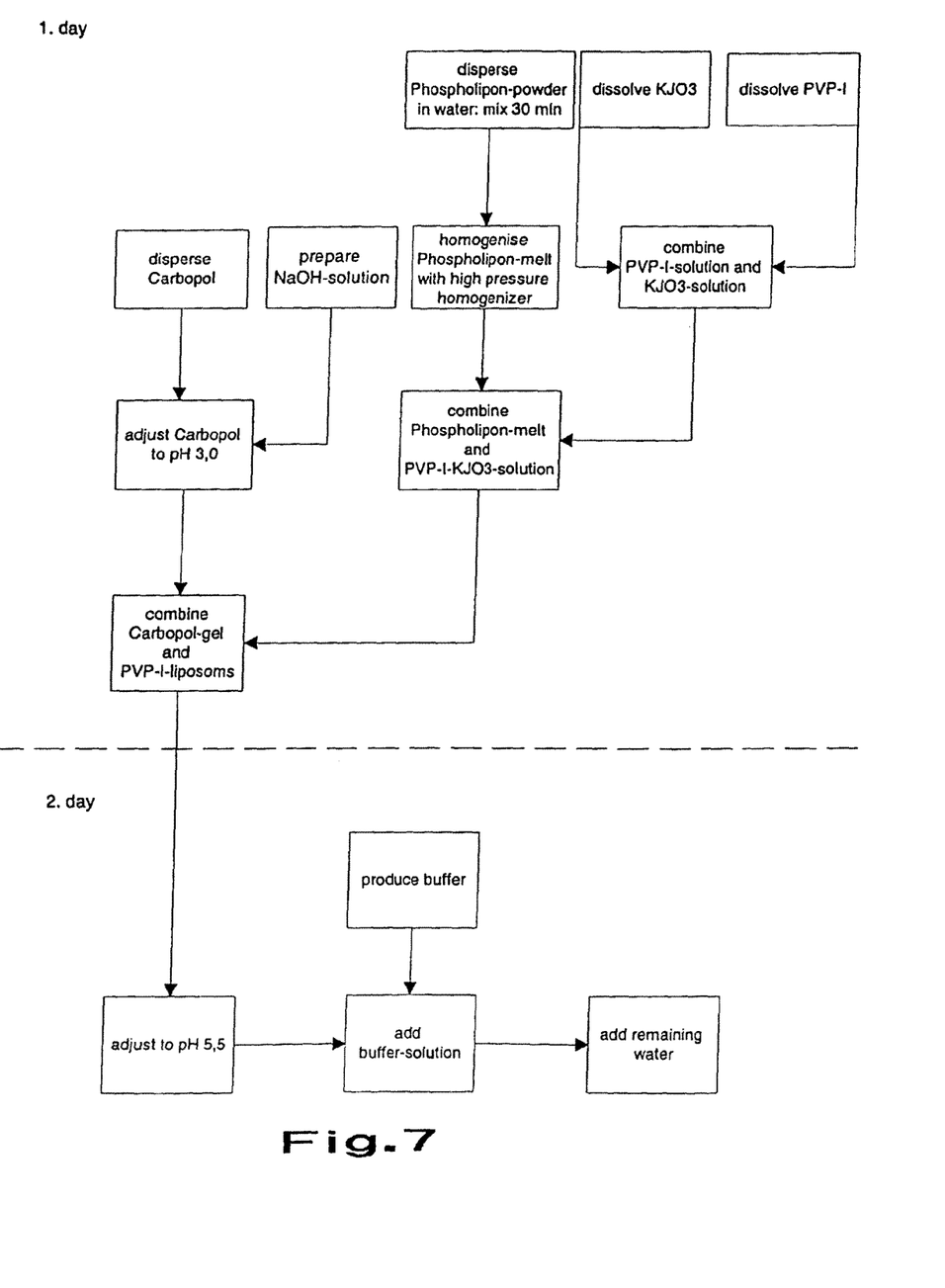
Figure 8:
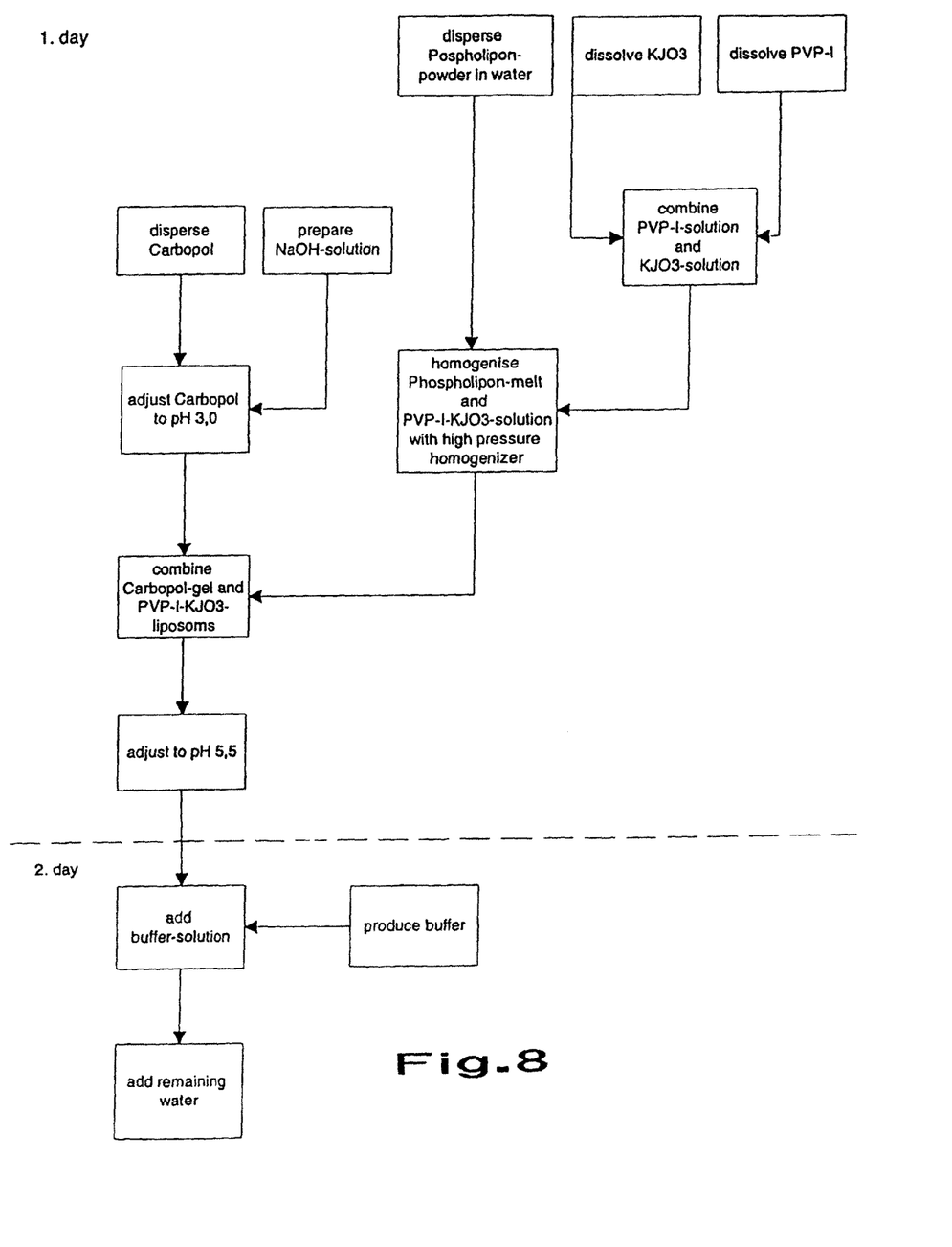

In Table 2, column 2 the exact order of steps and the parameters of each step are given (see also FIG. 1). Column 3 discusses non-exclusive alternatives. All steps were performed at room temperature except where indicated otherwise. All substances were of a purity grade common for pharmaceutical preparations such as described in the British Pharmacopeia.

TABLE II

| No. | Embodiment example VII | Alternatives |
|---|---|---|
| 1 | Carbopol 980 NF is mixed into $H_2O$ without agglomeration (Pos. B). Stirring for 30 min a approx. 30 upm (units per minute) in conventional stirrer. Visual control for Polyacrylic acid-agglomerates. If necessary, homogenize gel in conventional homogenisator for 2 min at 3000 upm. Subsequently stir gel for 30 min at 30 upm in conventional stirrer. Eventually control again for Polayacrylicacid-agglomerates. If present, remove them and stir again for 15 min at 30 upm. Eventually homogenize again. Let gel swell for at least 14 h. | Substances: Other gel-forming substances may be used. Homogenization time can vary: shorten to 1 min prolong to 10 min (caution! gel structure may be destroyed) Stirring time can be altered as desired. Only condition is that gel is free of agglomerates at the end. Swelling time may be altered from 15 min to 5 days. Preferably the gel has formed before other substances are added. Adjustment of pH to 2-8 may be performed at this stage. Adjustment to pH 3-6 is preferred. |
| 2 | Dissolve $H_2O$ and $KIO_3$ completely in a suitable vessel (Pos. C). Alternatively a 30-40% $KIO_3$ solution may be used. | $H_2O$-temperature may be adjusted to anywhere between ambient temperature and 100° C. $KIO_3$ is not obligatory. |
| 3 | Dissolve NaOH completely in $H_2O$ (Pos. G). | NaOH is used in concentrations common for pharmaceutical preparations. Other Bases or substances suggested by the supplier of the gel forming substances may also be used for formation of gel structure as e.g. KOH, Triethanol-amine, 2-Amino-2-methyl-1-propanol, tris(hydroacnemethyl)aminoethan, 2-hydroacnepropyl-ethylen-diamine, diisopropanolamine. |
| 4 | Mix PVP-iodine into $H_2O$ while stirring at 1000 upm in conventional stirrer (Pos. D). Stir mixture for further 60-70 min at 1000 upm until it is completely dissolved. | Stirring time and speed can be altered arbitrarily. Important: PVP-Iodine has to be dissolved completely. |
| 5 | Warm $H_2O$ to 65° C. while stirring with 1000 upm in conventional stirrer. Then add slowly Phospholipon ® 90 H (Pos. A). Take care that no agglomerates are formed. Stir dispersion for further 90 min at 65° C.-70° C. and 1000 upm. | Possible temperature range: 40° C.-120° C. 50° C.-75° C. is preferred because of phase transition temperature. Other liposome-forming materials or mixtures thereof may be used. Stirring time and speed: Is dependent on |

TABLE II-continued

| No. | Embodiment example VII | Alternatives |
|---|---|---|
| | Subsequently cool liposomal dispersion to ≤30° C. while stirring at 500 upm | equipment. A complete dispersion has to be achieved. Apparatus of the rotor/stator principle, high pressure homogenisators, ultrasound or extrusion technology may also be used for stirring. |
| 6 | By adding the NaOH-solution (No. 3) the gel is adjusted to a pH of 3.0 (±0.2). | Further processing to a gel may be feasible without pH pre-adjustment and is dependent on the gel-forming substance |
| 7 | The $KIO_3$ solution (No. 2) is added to the PVP-Iodine solution (No. 4) while stirring at 1000 upm. Stirring continued for at least 60 min. | Reaction between $KIO_3$ and PVP-iodine is time dependent. To ensure a complete reaction, the stirring time has to adapted accordingly. Thus, stirring time may be between 10 min and 2 h |
| 8 | The PVP-iodine-$KIO_3$-solution is pumped into the liposomal dispersion (No. 5). Subsequently it is stirred for 30 min at 1000 upm. | Stirring time is variable depending on until when an homogeneous mixture has formed. |
| 9 | The PVP-iodine-$KIO_3$-liposomes-dispesion is added to the gel (No. 6). It is stirred for 30 min at 30 upm. Subsequently homogenization is performed by forced circulation pumping for 2 min at 2800 upm. After checking for agglomerate, it may be homogenized for further 1-2 min. | Stirring time is variable depending on until when an homogeneous mixture has formed. Stirring time should be as short as possible so that gel structure gets not disrupted. |
| 10 | Remove agglomerates if present. Add 50.0 kg NaOH-solution (in the scale up, point 3) while stirring at 30 upm. Stir for further 30 min at 30 upm at ≤30° C. Cool if necessary. Determine pH and add additional NaOH until an pH of 5.5 (±0.2) is achieved. After each adding step stir for 20 min. After each adding step homogenize by circulation pressure pumping for 15 sec at 1000 upm. After adjustment of pH stir for further 15 min at 30 upm. Check pH and correct if necessary. After successful pH adjustment add remaining $H_2O$ amount which depends on the amount of NaOH used. | Adjust stirring time and speed to gel quality. Amounts of NaOH may vary. Adding of base by step wise adjustment until desired pH is achieved. |
| 11 | Mix buffer solution at 30° C. while stirring until it is completely dissolved (Pos. I). | Temperature can be raised to 40° C. Other suitable buffers may also be used. |
| 12 | Buffer solution is added to the product (No. 10) while stirring for 15 min at 30 upm. Degas by application of vacuum. | The desired product quality (storage stability) is achieved by addition of the buffer. Stirring time is variable depending on until when an homogeneous mixture has formed. Degasing may be achieved by other means than vacuum. |
| 13 | Add the remaining $H_2O$-amount (Pos. H) and stir for 30 min at 25 upm Optionally homogenization may be performed by circulation pressure pumping for 15 sec at 1000 upm. Stir for another 30 min. Check visually for agglomerates | Stirring time is variable depending on until when an homogeneous mixture has formed. |

Positions E and F of Table I are used for washing the $KIO_3$— and the PVP-iodine vessels (points 2 and 4 of Table II).

As mentioned above the Hydrogel-Formulation is produced according to the method set out in Table 2 and FIG. 1. Alternative methods become obvious from the flow charts of FIGS. 2 to 8. The individual steps may be performed as set out above.

This liposomal PVP-I gel is freeze dried subsequently. Samples of 10 g each are frozen at −20° C. for 22 h and subsequently dried at −40° C. and 0.5 mbar for 3 hours. The dry composition is filled in a polypropylene container for storage. One sample was mixed with X g of water by stirring with a spatula. The resulting mixture was the reconstituted hydrogel and ready for application.

We claim:

1. A storage stable package comprising a freeze-dried, iodophor-containing pharmaceutically acceptable liposome composition in a plastic material, paper or cardboard package, wherein the composition comprises at least one gel-forming substance selected from the group consisting of agar, an alginate, alginic acid, arabic gum, gelatine, starch, tragacanth gum, methylcellulose, hydroxyethylcellulose, carboxymethylcellulose, polyvinylpyrrolidone (PVP) and polyacrylic acid.

2. A storage stable package according to claim 1, wherein the package is a plastic bottle or container.

3. A storage stable package according to claim 1, wherein the iodophor is povidone iodine.

4. A storage stable package according to claim 1, wherein the composition does not contain a stabilizer selected from the group consisting of an iodide salt, an iodate salt and an alkanizing agent.

5. A storage stable package according to claim 1, wherein at least a part of the iodophor is encapsulated inside the liposome.

6. A storage stable package according to claim 2, wherein the plastic bottle or container is made of polypropylene (PP), Polyethylene (PE), cycloolefine copolymer (COC), silicone, polytetrafluoroethylene (PTFE), polyvinylchlorid (PVC), ethylene vinylalkohol (EVOH), polyethylene terephthalate (PET) or mixtures thereof.

7. A storage stable package according to claim 2, wherein the plastic bottle or container is made of a material that reacts with elemental iodine, gets stained by elemental iodine or elemental iodine leaches through the material, under storing conditions.

8. A storage stable package according to claim 1, wherein the composition additionally contains one or more anti-inflammatory agents which promotes the healing of wounds.

9. A storage stable package according to claim 8, wherein the anti-inflammatory agent is an germicidal agent, an antibiotic, a coricosteroid or a wound healing promoting agent.

10. A storage stable package according to claim 9, wherein the wound healing promoting agent comprises dexpanthenol, an allantoine, an azulene, a tannin, or a compound from the vitamin B series.

11. A storage stable package according to claim 1, wherein the liposome particles have, before they are dried, a substantially uniform size in the range between about 1 and about 100 µm.

12. A storage stable package according to claim 1, wherein the composition can be transformed to the applicable preparation upon mixing with a liquid pharmaceutically acceptable medium.

13. A storage stable package according to claim 12, wherein the liquid pharmaceutically acceptable medium comprises water, oil, an ointment basis substance or a gel forming substance.

14. A storage stable package according to claim 13, wherein the liposome, composition contains, as an additive and adjuvant, a conserving agent, an antioxidant or a consistency-forming additive.

15. A storage stable package according to claim 11, wherein the liposome carrier particles have, before they are dried, a substantially uniform size in the range between about 1 µm and about 70 µm.

16. A method of providing the storage stable package of claim 1, comprising the steps of:
   a. providing a iodophor containing particulate pharmaceutically acceptable liposome preparation, wherein the preparation comprises at least one gel-forming substance selected from the group consisting of agar, an alginate, alginic acid, arabic gum, gelatine, starch, tragacanth gum, methylcellulose, hydroxvethylcellulose, carboxymethylcellulose, polyvinylpyrrolidone (PVP) and polyacrylic acid,
   b. freeze-drying the iodophor containing pharmaceutically acceptable liposome preparation to obtain a dry composition, and
   c. placing the freeze-dried iodophor containing pharmaceutically acceptable liposome composition in the storage stable package, wherein the storage stable package is made of plastic material, paper or cardboard.

* * * * *

UNITED STATES PATENT AND TRADEMARK OFFICE
CERTIFICATE OF CORRECTION

| | | |
|---|---|---|
| PATENT NO. | : 9,078,822 B2 | Page 1 of 1 |
| APPLICATION NO. | : 13/371030 | |
| DATED | : July 14, 2015 | |
| INVENTOR(S) | : Mühlau et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

In the Claims:

In claim 14, on column 20, line 10, replace the phrase "the liposome, composition" with --- the liposome composition ---;

In claim 15, on column 20, line 14, replace the phrase "the liposome carrier particles" with --- the liposome particles ---;

In claim 16, on column 20, line 24, replace the word "hydroxvethylcellulose" with --- hydroxyethylcellulose ---.

Signed and Sealed this
Tenth Day of May, 2016

Michelle K. Lee
*Director of the United States Patent and Trademark Office*